(12) United States Patent
Schelberger et al.

(10) Patent No.: US 6,436,979 B1
(45) Date of Patent: Aug. 20, 2002

(54) FUNGICIDAL MIXTURES

(75) Inventors: Klaus Schelberger, Gönnheim; Maria Scherer, Landau; Reinhold Saur, Böhol-Iggelheim; Karl Eicken, Wachenheim; Hubert Sauter, Mannheim; Eberhard Ammermann, Heppenheim; Thomas Grote, Schifferstadt; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/674,542

(22) PCT Filed: Apr. 23, 1999

(86) PCT No.: PCT/EP99/02729

§ 371 (c)(1),
(2), (4) Date: Nov. 2, 2000

(87) PCT Pub. No.: WO99/56551

PCT Pub. Date: Nov. 11, 1999

(51) Int. Cl.[7] .......................... A01N 43/80; A01N 43/78

(52) U.S. Cl. ...................................... 514/372; 514/365

(58) Field of Search ................................. 514/372, 365

(56) References Cited

U.S. PATENT DOCUMENTS 4,829,085 A    5/1989   Wenderoth (List continued on next page.)

FOREIGN PATENT DOCUMENTS

| DE | 43 21897 | 1/1995 |
| DE | 195 31814 | 3/1997 |

(List continued on next page.)

OTHER PUBLICATIONS

JP 09323984—Derwent Abstr.

Primary Examiner—Edward J. Webman
(74) Attorney, Agent, or Firm—Keil & Weinkauf

(57) ABSTRACT

A fungicidal mixture, comprising at least one compound selected from a) [sic] carbamates of the formula I,

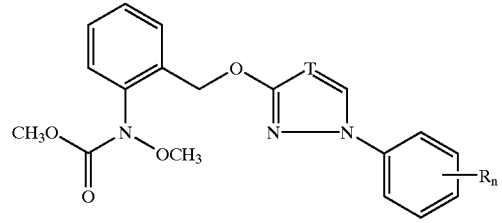

in which T is CH or N, n is 0, 1 or 2 and R is halogen, $C_1$–$C_4$-alkyl or $C_1$–$C_4$-haloalkyl, where the radicals R may be different if n is 2, $a_2$) the oxime ether carboxylate of the formula II

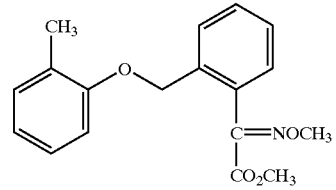

or $a_3$) the oxime ether carboxamide of the formula III,

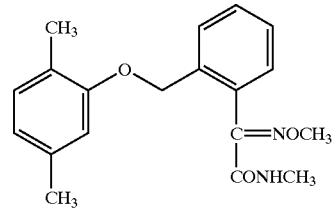

and b) a compound of the formula IV

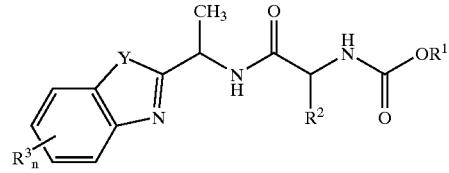

where the substituents $R^1$ to $R^3$ have the following meaning:
$R^1$ is $C_1$–$C_4$-alkyl, $C_2$–$C_4$-alkenyl, $C_2$–$C_4$-alkynyl, $C_1$–$C_4$-alkyl-$C_3$–$C_7$-cycloalkyl, where these radicals may carry substituents selected from halogen, cyano and $C_1$–$C_4$-alkoxy,
$R^2$ is $C_1$–$C_4$-alkyl or $C_1$–$C_4$-haloalkyl,
$R^3$ is hydrogen, halogen, $C_1$–$C_4$-alkyl, $C_1$–$C_4$-alkoxy, $C_1$–$C_4$-alkylthio, N—$C_1$–$C_4$-alkylamino, $C_1$–$C_4$-haloalkyl or $C_1$–$C_4$-haloalkoxy,
Y is O, S, $CHR^4$ or $NR^5$, where $R^4$ and $R^5$ may each have the meanings mentioned for $R^2$,
n is 0, 1, 2 or 3,
in a synergistically effective amount, and methods for controlling harmful fungi using these mixtures are described.

22 Claims, No Drawings

U.S. PATENT DOCUMENTS

| | | |
|---|---|---|
| 5,185,342 A | 2/1993 | Hayase et al. |
| 5,395,854 A | 3/1995 | Brand |
| 5,869,517 A | 2/1999 | Mueller |
| 5,922,899 A | 7/1999 | Wetterich |

FOREIGN PATENT DOCUMENTS

| | | | | |
|---|---|---|---|---|
| EP | 253 213 | 1/1988 | | |
| EP | 398 692 | 11/1990 | | |
| EP | 477 631 | 4/1992 | | |
| EP | 0775696 A1 | * 5/1997 | ......... | C07D/235/14 |
| EP | 775 696 | 5/1997 | | |
| WO | 96/01256 | 1/1996 | | |
| WO | 96/01258 | 1/1996 | | |
| WO | WO 97/40688 | * 11/1997 | | |
| WO | 98/08386 | 3/1998 | | |

* cited by examiner

FUNGICIDAL MIXTURES

The present invention relates to fungicidal mixtures which comprise at least one compound selected from a₁) carbamates of the formula I,

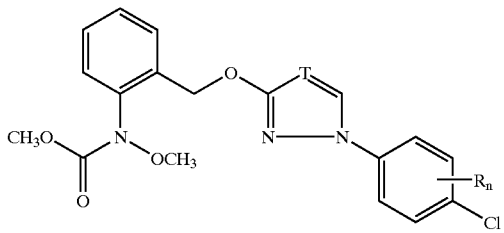

in which T is CH or N, n is 0, 1 or 2 and R is halogen, $C_1$–$C_4$-alkyl or $C_1$–$C_4$-haloalkyl, where the radicals R may be different if n is 2, a₂) the oxime ether carboxylate of the formula II

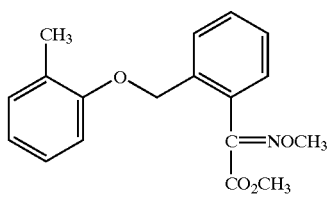

or a₃) the oxime ether carboxamide of the formula III,

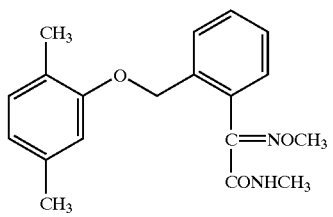

and b) at least one active compound of the formula IV,

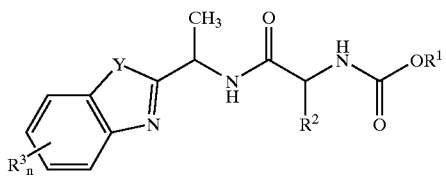

where the substituents $R^1$ to $R^3$ have the following meaning:

$R^1$ is $C_1$–$C_4$-alkyl, $C_2$–$C_4$-alkenyl, $C_2$–$C_4$-alkynyl, $C_1$–$C_4$-alkyl-$C_3$–$C_7$-cycloalkyl, where these radicals may carry substituents selected from the group consisting of halogen, cyano and $C_1$–$C_4$-alkoxy, and is also $C_1$–$C_4$-alkoxy, $R^2$ is $C_1$–$C_4$-alkyl or $C_1$–$C_4$-haloalkyl, $R^3$ is hydrogen, halogen, $C_1$–$C_4$-alkyl, $C_1$–$C_4$-alkoxy, $C_1$–$C_4$-alkylthio, N—$C_1$–$C_4$-alkylamino, $C_1$–$C_4$-haloalkyl or $C_1$–$C_4$-haloalkoxy, Y is O, S, $CHR^4$ or $NR^5$, where $R^4$ and $R^5$ may each have the meanings mentioned for $R^2$, n is 0, 1, 2 or 3, in a synergistically effective amount.

Moreover, the invention relates to methods for controlling harmful fungi using mixtures of the compounds I, II and/or III and IV and to the use of the compounds I, II and/or III and IV for preparing such mixtures.

The compounds of the formula I, their preparation and their action against harmful fungi are known from the literature (WO-A 96/01,256 and 96/01,258).

The compounds of the formulae II and III, their preparation and their action against harmful fungi are known from the literature (EP-A 253 213, EP-A 398 692 and EP-A 477631).

The compounds of the formula IV and also processes for their preparation are described in JP-A 09/323984. Moreover, they can be prepared using the processes described in DE 1 95 31 814.

It is an object of the present invention to provide mixtures which have improved activity against harmful fungi combined with a reduced total amount of active compounds applied (synergistic mixtures), with a view to reducing the application rates and to improving the activity spectrum of the known compounds.

We have found that this object is achieved by the mixtures defined at the outset. Moreover, we have found that better control of harmful fungi is possible by applying the compounds I and/or II and/or III and IV simultaneously, that is either together or separately, or by applying the compounds I and/or II and/or III and IV in succession then when the individual compounds are used.

The formula I represents in particular carbamates in which the combination of the substituents corresponds to a row of the following table:

TABLE 1

| NO. | T | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |

TABLE 1-continued

| NO. | T | $R_n$ |
|---|---|---|
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

Particular preference is given to the compounds I.12, I.23, I.32 and I.38.

In relation to the C=Y or C=CH or C=N double bonds, the compounds of the formulae I to III can exist in the E or Z configuration (in relation to the carboxylic acid function). Accordingly, they can be used in the mixture according to the invention in each case either as pure E or Z isomers or as E/Z isomer mixtures. The E/Z isomer mixture or the Z isomer is preferably used, the Z isomer being particularly preferred.

The C=N double bonds of the oxime ether groups in the side chain of the compounds I to III can exist in each case as pure E or Z isomers or as E/Z isomer mixtures. The compounds I to III can be used in the mixtures according to the invention both as isomer mixtures and as pure isomers. With a view to their use, compounds I to III which are particularly preferred are those where the terminal oxime ether group in the side chain is present in the cis configuration ($OCH_3$ to ZR').

Owing to their basic character, the compounds I to III are capable of forming salts or adducts with inorganic or organic acids or with metal ions.

Examples of inorganic acids are hydrohalic acids such as hydrofluoric acid, hydrochloric acid, hydrobromic acid and hydroiodic acid, sulfuric acid, phosphoric acid, carbonic acid and nitric acid.

Suitable organic acids are, for example, formic acid, and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals with 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals with 1 to 20 carbon atoms), arylphosphonic acids or aryldiphosphonic acids (aromatic radicals, such as phenyl and naphthyl, which carry one or two phosphonic acid radicals), it being possible for the alkyl or aryl radicals to carry further substituents, e.g. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the second main group, in particular calcium and magnesium, of the third and fourth main group, in particular aluminum, tin and lead, and of the first to eighth subgroup, in particular chromium, manganese, iron, cobalt, nickel, copper and zinc, and others. Particular preference is given to the metal ions of the elements of the subgroups of the fourth period. The metals can exist in the various valences which they can assume.

Among the compounds of the formula IV, preference is given to those in which $R^1$ is $C_1$–$C_4$-alkyl (methyl, ethyl, n- and i-propyl and t-butyl), $C_1$–$C_4$-alkylene-$C_3$–C7-cycloalkyl, $C_1$–$C_4$-alkenyl (in particular ethenyl, propenyl and butenyl which may be substituted in particular by halogen (preferably Cl)), propynyl, cyanomethyl and methoxymethyl. Among the $C_1$–$C_4$-alkylene-$C_3$–$C_7$-cycloalkyl substituents, particular preference is given to methylene-substituted compounds, in particular to methylenecyclopropyl, methylenecyclopentyl, methylenecyclohexyl and methylenecyclohexenyl. The rings of these substituents may be substituted, preferably by halogen. Particular preference is given to i-propyl.

A preferred substituent $R^2$ is $C_1$–$C_4$-alkyl (in particular methyl, ethyl, i-propyl or n-, i- or t-butyl). Particular preference is given to i-propyl.

Preferred substituents $R^3$ and $R^4$ are hydrogen, F, Cl, methyl, ethyl, methoxy, thiomethyl and N-methylamino, in particular F or Cl.

Preferred compounds of the formula IV are shown in JP-A 09/329984, which has already been mentioned. Particular preference is given to the compound of the formula IV/1.

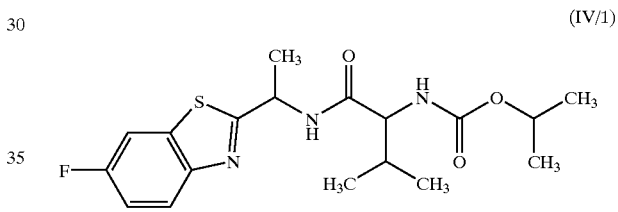

(IV/1)

When preparing the mixtures, it is preferred to employ the pure active compounds I, II and/or III and IV, with which further active compounds against harmful fungi or other pests, such as insects, arachnids or nematodes, or else herbicidal or growth-regulating active compounds or fertilizers can be admixed as required.

The mixtures of the compounds I, II and/or III and IV, or the simultaneous joint or separate use of the compounds I, II and/or III and IV, have outstanding action against a wide range of phytopathogenic fungi, in particular from the classes of the Ascomycetes, Deuteromycetes, Phycomycetes and Basidiomycetes. Some of them act systemically and are therefore also suitable for use as foliar and soil-acting fungicides.

They are especially important for controlling a large number of fungi in a variety of crop plants, such as cotton, vegetable species (for example cucumbers, beans and cucurbits), barley, grass, oats, coffee, maise, fruit species, rice, rye, soya, grapevine, wheat, ornamentals, sugarcane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugarcane, *Venturia inaequalis* (scab) in apples, Helminthosporium species in cereals, *Septoria nodorum* in wheat, *Botrytis cinerea* (gray mold) in strawberries, vegetables, ornamentals and grapevines, *Cercospora arachidicola* in groundnuts, *Pseudo-cercosporella herpotrichoides* in wheat and barley, *Pyricularia oryzae* in rice, *Phytophthora infestans* in potatoes and tomatoes, Pseudoperonospora species in cucurbits and hops, *Plasmopara viticola* in grapevines, Alternaria species in vegetables and fruit and Fusarium and Verticillium species.

Furthermore, they can be used in the protection of materials (e.g. in the protection of wood), for example against *Paecilomyces variotii*.

The compounds I, II and/or III and IV can be applied simultaneously, either together or separately, or in succession, the sequence, in the case of separate application, generally not having any effect on the control results.

The compounds I, II and/or III and IV are usually applied in a weight ratio of from 0.01:1 to 1:1, preferably from 0.03:1 to 0.5:1, in particular from 0.05:1 to 0.5:1 (IV:I, II and/or III).

Depending on the nature of the desired effect, the application rates of the mixtures according to the invention are, for the compounds I, II and/or III, from 0.005 to 0.5 kg/ha, preferably from 0.05 to 0.5 kg/ha, in particular from 0.05 to 0.2 kg/ha.

Correspondingly, the application rates for the compounds IV are usually from 0.001 to 0.5 kg/ha, preferably from 0.001 to 0.1 kg/ha, in particular from 0.005 to 0.05 kg/ha.

For seed treatment, the application rates of the mixture are generally from 0.001 to 100 g/kg of seed, preferably from 0.01 to 50 g/kg, in particular from 0.01 to 10 g/kg.

If phytopathogenic harmful fungi are to be controlled, the separate or joint application of the compounds I and II or of the mixtures of the compounds I, II and/or III and IV is effected by spraying or dusting the seeds, the plants or the soils before or after sowing of the plants, or before or after plant emergence.

The fungicidal synergistic mixtures according to the invention, or the compounds I, II and/or III and IV, can be formulated for example in the form of ready-to-spray solutions, powders and suspensions or in the form of highly concentrated aqueous, oily or other suspensions, dispersions, emulsions, oil dispersions, pastes, dusts, materials for scattering or granules, and applied by spraying, atomizing, dusting, scattering or watering. The use form depends on the intended purpose; in any case, it should ensure as fine and uniform a distribution as possible of the mixture according to the invention.

The formulations are prepared in a manner known per se, e.g. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols or fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene [sic], lauryl alcohol polyglycol ether acetate, sorbitol esters, lignosulfite waste liquors or methylcellulose.

Powders, materials for scattering and dusts can be prepared by mixing or jointly grinding the compounds I and II or III or IV or the mixture of the compounds I and II, III or IV with a solid carrier.

Granules (e.g. coated granules, impregnated granules or homogeneous granules) are usually prepared by binding the active compound, or active compounds, to a solid carrier.

Fillers or solid carriers are, for example, mineral earths, such as silica gel, silicic acids, silica gels [sic], silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas and products of vegetable origin, such as cereal meal, tree bark meal, wood meal and nutshell meal, cellulose powders or other solid carriers.

The formulations generally comprise from 0.1 to 95% by weight, preferably from 0.5 to 90% by weight, of one of the compounds I, II, III and/or IV or of the mixture of the compounds I, II and/or III and IV. The active compounds are employed in a purity of from 90% to 100%, preferably from 95% to 100% (according to NMR or HPLC spectrum).

The compounds I, II and/or III or IV, or the mixtures or the corresponding formulations, are applied by treating the harmful fungi, the plants, seeds, soils, areas, materials or spaces to be kept free from them with a fungicidally effective amount of the mixture, or of the compounds I, II and/or III and IV in the case of separate application. Application can be effected before or after infection by the harmful fungi.

The fungicidal activity of the compound and of the mixtures can be demonstrated by the following experiments:

The active compounds, separately or together, are formulated as a 10% emulsion in a mixture of 70% by weight of cyclohexanone, 20% by weight of Nekanil® LN (Lutensol® AP6, wetting agent having emulsifying and dispersing action, based on ethoxylated alkylphenols) and 10% by weight of Emulphor® EL (Emulan® EL, emulsifier based on ethoxylated fatty alcohols) and diluted with water to give the desired concentration.

Evaluation is carried out by determining the infected leaf areas in percent. These percentages are converted into efficacies. The expected efficacies of the active compound mixtures are determined using Colby's formula [R. S. Colby, Weeds 15, 20–22 (1967)] and compared with the observed efficacies. Colby's formula:

$$E = x + y + z - x \cdot y \cdot z / 100$$

E expected efficacy, expressed in % of the untreated control, when using the mixture of the active compounds A, B and C at the concentrations a, b and c x efficacy, expressed in % of the untreated control, when using active compound A at a concentration of a y efficacy, expressed in % of the untreated control, when using active compound B at a concentration of b z efficacy, expressed in % of the untreated control, when using active compound C at a concentration of c The efficacy (E) is calculated as follows using Abbot's formula:

$$E = (1 - \alpha) \cdot 100 / \beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants are not infected.

Use Example 1—Activity against Phytophthora infestans on tomatoes

Leaves of potted plants cv. "GroBe Fleischtomate" were sprayed to runoff point with an aqueous suspension which had been prepared from a stock solution of 10% of active compound, 63% of cyclohexanone and 27% of emulsifier. The next day, the leaves were infected with an aqueous zoospore suspension of *Phytophthora infestans*. The plants were subsequently placed in a water-vapor-saturated chamber at 16–18° C. After 6 days, the late blight on the untreated but infected control plants had developed to such an extent that the infection could be determined visually in %.

The visually determined values for the percentage of infected leaf areas were converted into efficacies as percent of the untreated control. An efficacy of 0 means the same degree of infection as in the untreated control, an efficacy of 100 means 0% infection. The expected efficacies for active compound combinations were determined using Colby's formula (Colby, S. R. "Calculating synergistic and antagonistic responses of herbicide combinations", Weeds 15 (1967), 20–22) and compared with the observed efficacies.

The test results are shown in Tables 2 and 3 below.

TABLE 2

Comparative experiments

| Ex. | Active compound | Conc. in the spray liquor in ppm | Efficacy in % of the untreated control |
|---|---|---|---|
| 1C | Compound I.32 from Tab. 1 | 0.25<br>0.06 | 55<br>10 |
| 2C | Compound I.38 from Table 1 | 0.25<br>0.06 | 33<br>0 |
| 3C | Compound II | 0.06 | 10 |
| 4C | Compound III | 0.25<br>0.06 | 33<br>0 |
| 5C | Compound IV/1 | 0.06 | 21 |
| 6C | Control untreated | 89% infection | 0 |

TABLE 3

Mixtures according to the invention

| Ex. | Mixtures according to the invention (conc. in ppm) | Observed efficacy | Calculated efficacy* |
|---|---|---|---|
| 7 | 0.06 I.32 + 0.06 IV/1 | 78 | 29 |
| 8 | 0.25 I.32 + 0.06 IV/1 | 94 | 65 |
| 9 | 0.06 I.38 + 0.06 IV/1 | 83 | 21 |
| 10 | 0.25 I.38 + 0.06 IV/1 | 94 | 47 |
| 11 | 0.25 II + 0.06 IV/1 | 78 | 29 |
| 12 | 0.06 III + 0.06 IV/1 | 83 | 21 |
| 13 | 0.25 III + 0.06 IV/1 | 83 | 47 |

* according to Colby's formula

The test results show that the observed efficacy is in all cases higher than the efficacy which had been calculated beforehand using Colby's formula.

We claim:

1. A fungicidal composition comprising as active components a) at least one compound selected from a group consisting of $a_1$) carbamates of formula I,

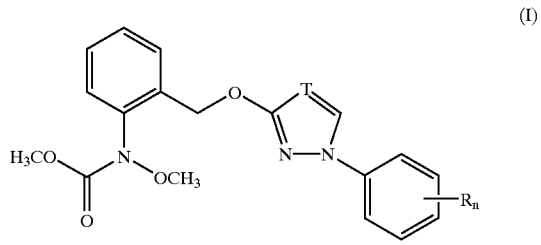

wherein T is CH or N, n is 0, 1 or 2 and R is halogen, $C_1$–$C_4$-alkyl or $C_1$–$C_4$-haloalkyl, and the radicals R are identical or different when n is 2, $a_2$) an oxime ether carboxylate of formula II

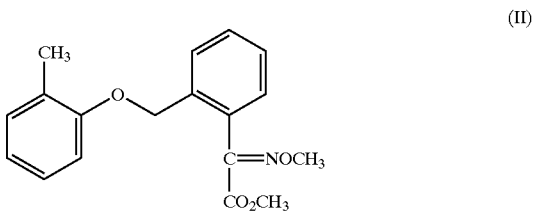

and $a_3$) an oxime ether carboxamide of formula III,

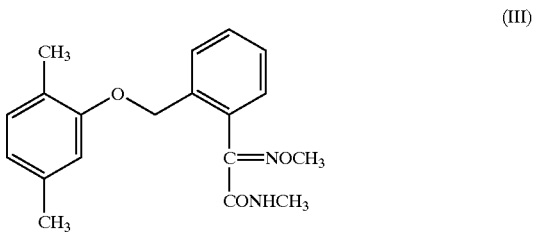

and b) a compound of formula IV

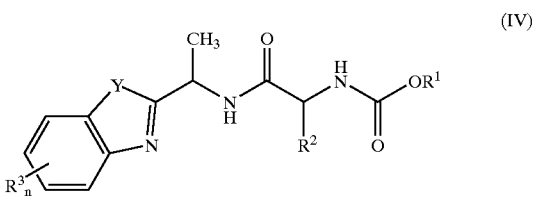

wherein $R^1$ is $C_1$–$C_4$-alkyl, $C_2$–$C_4$-alkenyl, $C_2$–$C_4$-alkynyl, $C_1$–$C_4$-alkyl-$C_3$–$C_7$-cycloalkyl, where these radicals are unsubstituted or carry substituents selected from the group consisting of halogen, cyano and $C_1$–$C_4$-alkoxy, or is $C_1$–$C_4$-alkoxy, $R^2$ is $C_1$–$C_4$-alkyl or $C_1$–$C_4$-haloalkyl, $R^3$ is hydrogen, halogen, $C_1$–$C_4$-alkyl, $C_1$–$C_4$-alkoxy, $C_1$–$C_4$-al-kylthio, N—$C_1$–$C_4$-alkylamino, $C_1$–$C_4$-haloalkyl or $C_1$–$C_4$-haloalkoxy, Y is O, S, $CHR^4$ or $NR^5$, where $R^4$ and $R^5$ have the meanings mentioned for $R^2$, n is 0, 1, 2 or 3, and wherein the active components are present in synergistically effective amounts.

2. The composition defined in claim 1, comprising as component b) a compound of formula IV/1

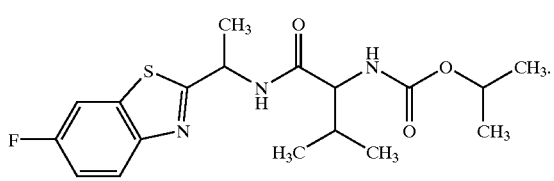
(IV/1)

3. A method for controlling phytopathogenic fungi, which comprises treating the phytopathogenic fungi, their habitat or plants, seeds, soils, areas, materials or spaces to be kept free from said fungi with an effective amount of the composition defined in claim 1.

4. The method of claim 3, wherein the active component (a) is applied in an amount of from 0.005 to 0.5 kg/ha.

5. The method of claim 3, wherein the active component (b) is applied in an amount of from 0.001 to 0.5 kg/ha.

6. The composition of claim 2, wherein T is CH and $R_n$ is 4-Cl.

7. The method of claim 5, wherein compound (I), T is CH and $R_n$ is 4-Cl.

8. The composition defined in claim 1, wherein the active components (b) and (a) are present in a weight ratio of from 0.01:1 to 1:1.

9. The method of claim 3, wherein the active components (b) and (a) are applied in a weight ratio of from 0.01:1 to 1:1.

10. A fungicidal composition comprising as active components $a_1$) at least one carbamate of formula I,

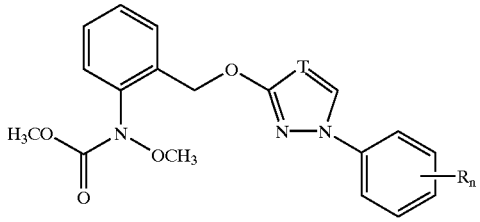
(I)

wherein T is CH or N, n is 0, 1 or 2 and R is halogen, $C_1$–$C_4$-alkyl or $C_1$–$C_4$-haloalkyl, and the radicals R are identical or different when n is 2, and b) a compound of formula IV

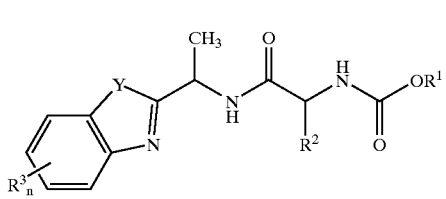
(IV)

wherein
$R^1$ is $C_1$–$C_4$-alkyl, $C_2$–$C_4$-alkenyl, $C_2$–$C_4$-alkynyl, $C_1$–$C_4$-alkyl-$C_3$–$C_7$-cycloalkyl, where these radicals are unsubstituted or carry substituents selected from the group consisting of halogen, cyano and $C_1$–$C_4$-alkoxy, or is $C_1$–$C_4$-alkoxy,
$R^2$ is $C_1$–$C_4$-alkyl or $C_1$–$C_4$-haloalkyl,
$R^3$ is hydrogen, halogen, $C_1$–$C_4$-alkyl, $C_1$–$C_4$-alkoxy, $C_1$–$C_4$-alkylthio, N—$C_1$–$C_4$-alkylamino, $C_1$–$C_4$-haloalkyl or $C_1$–$C_4$-haloalkoxy, Y is O, S, $CHR^4$ or $NR^5$, where $R^4$ and $R^5$ have the meanings mentioned for $R^2$,
n is 0, 1, 2 or 3,
and wherein the active components are present in synergistically effective amounts.

11. The composition defined in claim 10, wherein component (b) is a compound of formula IV/1

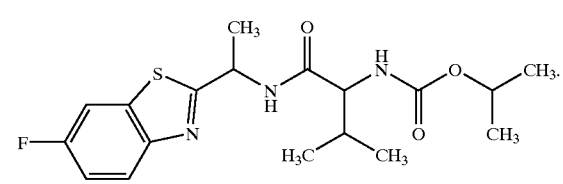
(IV/1)

12. The composition defined in claim 10, wherein the active component (a) comprises, in addition to the carbamate of formula (I), an effective amount of an oxime ether compound of formula II or III

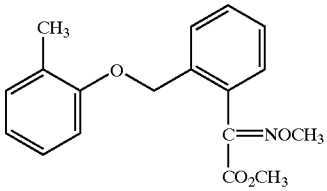
(II)

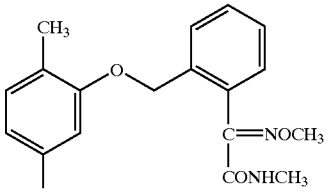
(III)

or a combination thereof.

13. The composition defined in claim 12, wherein component (b) is a compound of formula IV/1

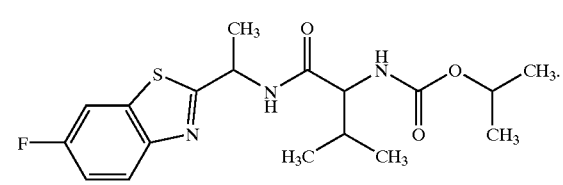
(IV/1)

14. The composition defined in claim 11, wherein the active components (b) and (a) are present in a weight ratio of from 0.01:1 to 1:1.

15. The composition defined in claim 13, wherein the active components (b) and (a) are present in a weight ratio of from 0.01:1 to 1:1.

16. A method for controlling phytopathogenic fungi, which comprises treating the phytopathogenic fungi, their habitat or plants, seeds, soils, areas, materials or spaces to be kept free from said fungi with an effective amount of the composition defined in claim 10.

17. The method of claim 16, wherein component (b) is a compound of formula IV/1

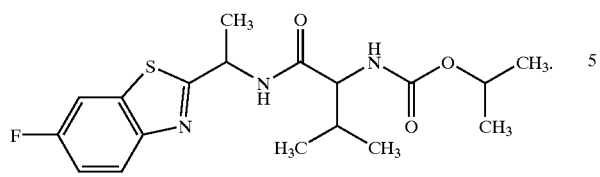 (IV/1)

18. The method of claim 16, wherein the active component (a) comprises, in addition to the carbamate of formula (I), an effective amount of an oxime ether carboxylate of formula II or III

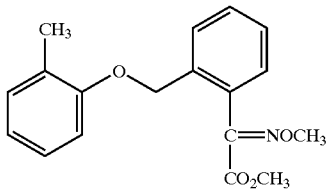 (II)

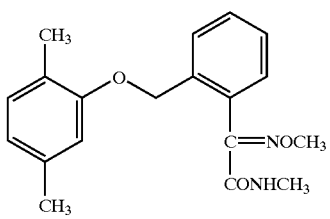 (III)

or a combination thereof.

19. The method of claim 18, wherein component (b) is a compound of formula IV/1

(IV/1)

20. The method of claim 16, wherein the active components (b) and (a) are applied in a weight ratio of from 0.01:1 to 1:1.

21. The method of claim 16, wherein the active component (a) is applied in an amount of from 0.005 to 0.5 kg/ha.

22. The method of claim 16, wherein the active component (b) is applied in an amount of from 0.001 to 0.5 kg/ha.

* * * * *

UNITED STATES PATENT AND TRADEMARK OFFICE
CERTIFICATE OF CORRECTION

PATENT NO. : 6,436,979 B1
DATED : August 20, 2002
INVENTOR(S) : Schelberger et al.

It is certified that error appears in the above-identified patent and that said Letters Patent is hereby corrected as shown below:

Title page,
ABSTRACT,
Line 1, "a) [sic]" should be -- $a_1$) --;
Line 2, after formula (I), "$C_l$-$C_4$-" should be -- $C_1$-$C_4$- --;
Lines 6 and 9, after formula (IV), "$C_l$-$C_4$-" should be -- $C_1$-$C_4$- --.

Column 8,
Line 61, "al-kylthio" should be -- alkylthio --.

Column 9,
Cancel claims 6 and 7.

Signed and Sealed this

Twelfth Day of November, 2002

*Attest:*

*Attesting Officer*

JAMES E. ROGAN
*Director of the United States Patent and Trademark Office*